United States Patent [19]

Matsumura et al.

[11] Patent Number: 4,904,663
[45] Date of Patent: Feb. 27, 1990

[54] N-(2-OXPYRROLIDIN-1-YL-)ACETYL)PIPERAZINE DERIVATIVES AND DRUG FOR SENILE DEMENTIA

[75] Inventors: Hiromu Matsumura, Hyogo; Hiroshi Hashizume, Osaka; Akira Matsushita, Hyogo; Masami Eigyo, Nara, all of Japan

[73] Assignee: Shionogi & Co., Ltd., Osaka, Japan

[21] Appl. No.: 221,450

[22] Filed: Jul. 15, 1988

[30] Foreign Application Priority Data

Jul. 15, 1987 [JP] Japan ................... 62-178064

[51] Int. Cl.$^4$ ............... A61K 31/495; C07D 403/06; C07D 401/14; C07D 403/14
[52] U.S. Cl. ........................ 514/252; 544/360; 544/372
[58] Field of Search .......... 544/372; 514/252; 548/187

[56] References Cited

U.S. PATENT DOCUMENTS

| 4,221,789 | 9/1980 | Rodriguez et al. | 544/372 |
| 4,372,960 | 2/1983 | L'Italien | 544/372 |
| 4,476,308 | 10/1984 | Aschwanden et al. | 544/372 |
| 4,668,687 | 5/1987 | Yevich et al. | 514/252 |

FOREIGN PATENT DOCUMENTS 089900 9/1983 European Pat. Off. .
203743 12/1986 European Pat. Off. .

OTHER PUBLICATIONS

Vedrilla, Chemical Abstracts, vol. 99, No. 88230 (1983).
Yevich et al., Chemical Abstracts, vol. 105, No. 172506 (1986).
Veda et al., Chemical Abstracts, vol. 106, No. 67300 (1987).

Primary Examiner—Mukund J. Shah
Assistant Examiner—L. Bernhardt
Attorney, Agent, or Firm—Wenderoth, Lind & Ponack

[57] ABSTRACT

A compound of the formula:

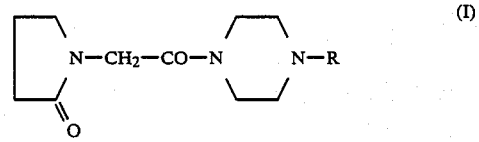

(wherein R is $-SO_2R^1$ or $-CONHR^2$; $R^1$ is $C_1-C_5$ alkyl, $C_8-C_{12}$ phenylalkenyl, amino, dimethylamino, optionally substituted $C_8-C_{12}$ aryl, or 5- or 6-membered heterocyclic group including at least one hetero atom selected from the group consisting of N, S, and O; $R^2$ is amino, $C_1-C_8$ alkylamino, $C_1-C_8$ alkyl, or optionally substituted $C_8-C_{12}$ aryl) or its pharmaceutically acceptable acid-addition salt, being useful as a drug for senile dementia, psychotropic, or antiamnesia agent is provided through several routes.

18 Claims, No Drawings

N-(2-OXPYRROLIDIN-1-YL-)ACETYL)PIPERAZINE DERIVATIVES AND DRUG FOR SENILE DEMENTIA

BACKGROUND OF THE INVENTION

This invention relates to N-[(2-oxopyrrolidin-1-yl)acetyl]piperazine derivatives. More particularly, this invention is directed to N-[(2-oxopyrrolidin-1-yl)acetyl]piperazine derivatives which have been found to be particularly available as a drug for senile dementia, psychotropic, and/or antiamnesia agent, to their preparation, to their use and to pharmaceutical formulations containing the compounds.

N-[(2-Oxopyrrolidin-1-yl)acetyl]piperazine derivatives have heretofore been known as useful antiamnesia agets, for example, in GB Unexamd. Pat. Publn. No. 2162843-A and EP Pat. Publn. No. 89900-B.

The inventors of the present invention have been studying antiamnesia agents of the piperazine family including such compounds. Thus, the present invention has been established.

The compounds of the present invention can be applicable for treating some kinds of senile dementia.

SUMMARY OF THE INVENTION

According to the present invention, there is provided an N-[(2-oxopyrrolidin-1-yl)acetyl]piperazine derivative of the formula

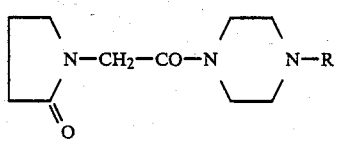

(wherein R is $-SO_2R^1$ or $-CONHR^2$; $R^1$ is $C_1-C_5$ alkyl, $C_8-C_{12}$ phenylalkenyl, amino, dimethylamino, optionally substituted $C_6-C_{12}$ aryl, or 5- or 6-membered heterocyclic group including at least one hetero atom selected from the group consisting of N, S, and O; $R^2$ is amino, $C_1-C_5$ alkylamino, $C_1-C_5$ alkyl, or optionally substituted $C_6-C_{12}$ aryl) or its pharmaceutically acceptable acid-addition salt.

The terms used in the above definition are explained below.

As the alkyl, methyl, ethyl, n-propyl, isopropyl, n-butyl, sec-butyl, isobutyl, tert-butyl, n-pentyl, and isopentyl are exemplified.

As the phenylalkenyl, styryl, phenylpropenyl, phenylbutenyl, and phenylpentenyl are exemplified.

As the aryl, phenyl, α-naphthyl, and β-naphthyl are exemplified.

As the heterocyclic group, thienyl, furyl, pyridyl, and pyrimidinyl are exemplified.

As the substituent which may be present an aryl, the alkyl above-illustrated alkoxy, halogen, acetylamino, and nitro are exemplified.

As the halogen, chlorine, fluorine, bromine, and iodine are indicated.

As the alkoxy, methoxy, ethoxy, and propoxy are illustrated.

The compound (I) of this invention is mainly prepared in accordance with the scheme shown below.

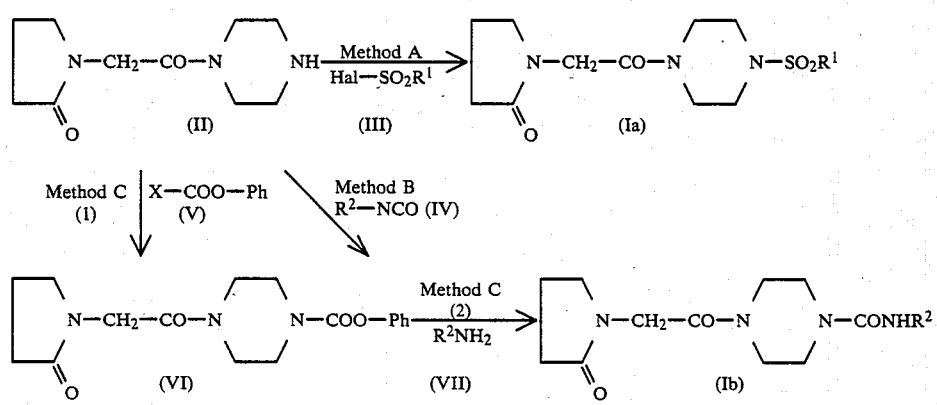

(wherein Hal and X each is halogen; $R^1$ and $R^2$ have the same meaning as defined abve. In method B, however, $R^2$ is alkyl or optionally substituted aryl.)

Method A

The compound (II) is allowed to react with sulfonyl halide (III) in an appropriate solvent to obtain a compound (Ia).

As the solvent, any inert organic solvent that can dissolve the reaction agent can be used. For example, aromatic solvents such as benzene, toluene, and xylene; alkanols such as methanol, ethanol, and isopropanol; ethers such as dioxane, tetrahydrofuran, diethylene glycol, diethyl ether, and dibutyl ether; dimethylformamide, and dimethyl sulfoxide can be used.

Further the reaction may be accelerated by adding a tertiary amine such as triethylamine or pyridine as an acceptor of an acid.

The reaction is carried out at a temperature from $-20°$ to $100°$ C., preferably $-5°$ to $30°$ C.

Method B

The compound (II) is allowed to react with an isocyanate (IV) in an appropriate solvent to obtain an objective compound (Ib). As the solvent, methanol, ethanol, benzene, chloroform, dichloromethane, and carbon tetrachloride may be used.

The reaction is carried out at a temperature from $-10°$ to $100°$ C., preferably around room temperature (1° to 30° C.).

Method C (1) The compound (II) is allowed to react with phenyl halogenoformate (V) in an appropriate solvent to obtain a compound (VI).

As the solvent, methanol, ethanol, benzene, chloroform, dichloromethane, and carbon tetrachloride may be used, and as the acceptor of an acid, bases such as triethylamine or pyridine can be used.

The reaction is carried out at a temperature from −10° to 100° C., preferably around room temperature.

(2) The compound (VI) obtained in the preceding step (1) is allowed to react with the amine (VII) to obtain an objective compound (Ib).

The reaction is carried out at a temperature from 50° to 150° C., preferably around 100° C.

Aside from above method A to method C, the following method are indicated as the synthesis of the objective compound (I).

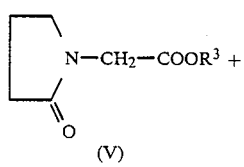
(V)

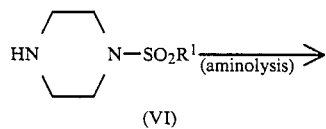
(VI)

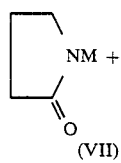
(I)

(wherein $R^1$ has the same meaning as defined above; $R^3$ is $C_1$–$C_3$ alkyl.)

(b)

NM +
(VII)

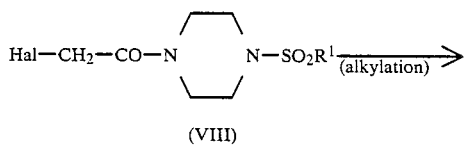
(VIII)

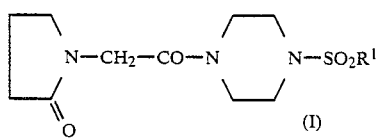
(I)

(wherein $R^1$ has the same meaning as defined above; Hal is halogen; M is a metal atom (e.g. sodium potassium)).

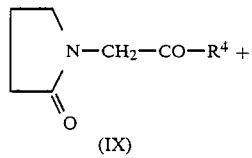
(IX)

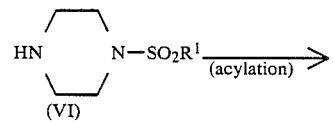
(VI)

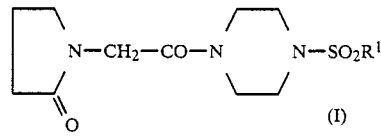
(I)

(wherein $R^1$ has the same meaning as defined above; $R^4$ is hydroxy or halogen.)

The starting material (II) is produced, for example, in the following process.

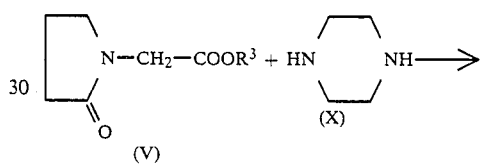
(V) (X)

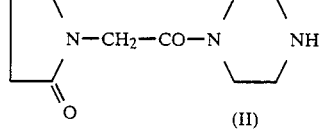
(II)

(wherein $R^5$ has the same meaning as defined above.)

The compound (I) can be converted into its pharmaceutically acceptable acid addition salt. Such acids illustratively include inorganic acids such as hydrochloric acid, sulfuric acid, phosphoric acid, nitric acid, hydrobromic acid, and hydrogen iodide and organic acids such as acetic acid, maleic acid, malic acid, citric acid, lactic acid, succinic acid, and methanesulfonic acid.

The comound (I) of this invention is effective for treating patients suffering from senile dementia, psychosis, or amnesia and useful as a drug for senile dementia, psychotropic, or antiamnesia agent.

The objective compound (I) of this invention can be administered to humans or animals either orally or parenterally. For example, the compound (I) may be orally administered in the form of tablets, granules, powder, capsules or liquid, or parenterally as injection or suppository. These preparations are manufactured in a known process by using additives such as diluents, binders, disintegrators, lubricants, stabilizers, corrigents, suspenders, dispersants, solubilizers and antiseptics. As the diluents, lactose, sucrose, starch, cellulose, and sorbit; as the binders, gum arabic, gelatin, and polyvinylpyrrolidone; and as the lubricants magnesium stearate, talc, and silica gel are exemplified, respectively. When the objective compound (I) of this invention is used in the therapy of senile dementia, a daily dose of about 0.01 to 20 mg/kg may be orally or parenterally administered in once or several times.

Embodiments of this invention are illustrated below by indicating Examples, Referential Examples, and Preparations.

The abbreviations used in the Examples, Referential Examples, and Tables have the following meanings.

Me: methyl, Et: ethyl, i-Pr: i-propyl, n-Bu: n-butyl, Ac: acetyl, MeOH: methanol, EtOH: ethanol, Et$_2$O: diethyl ether, Et$_3$N: triethylamine.

EXAMPLE 1

1-[(2-Oxopyrrolidinyl-1-yl)acetyl]-4-(4-methoxybenzenesulfonyl)piperazine

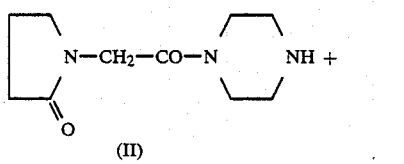

(II)

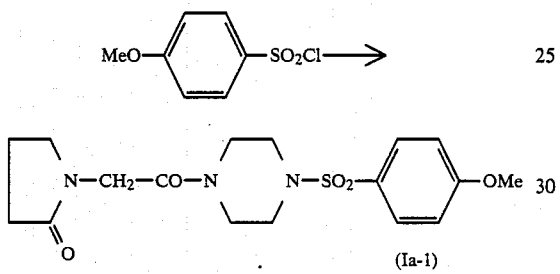

(Ia-1)

1.030 g (4.88 mmol) of [(2-oxopyrrolidinyl-1-yl)acetyl]piperazine (II) was dissolved in 15 ml of dichloromethane, and 1.108 g (5.36 mmol) of 4-methoxybenzenesulfonyl chloride and 0.748 ml (5.36 mmol) of triethylamine were added to the mixture with stirring under ice-cooling and the mixture was stirred for 5 hr. and 45 min. at room temperature and diluted with CH$_2$Cl$_2$. The solution was washed with diluted HCl, water, aqueous NaHCO$_3$, and water, respectively and was dried. After evaporating the solvent, the residue was subjected to silica gel column chromatography (silica gel: 91 g), and was eluted with CHCl$_3$—MeOH (30:1 to 9:1 v/v). 1.63 g of crystals obtained from the eluted fraction was recrystallized from MeOH, whereby 1.339 g of the objective compound (yield: 72.0%) was obtained as prisms.

Anal. Calcd. (%) for C$_{17}$H$_{23}$N$_3$O$_5$S: C, 53.53; H, 6.08; N, 11.02; S, 8.41. Found (%): C, 53.30; H, 6.06; N, 10.97; S, 8.29.

IR (Nujol): 3082, 1687, 1668, 1598, 1578, 1498, 1458, 1448, 1408 cm$^{-1}$.

NMR (CDCl$_3$—CD$_3$OD=4:1 v/v): δ 1.9–2.2 (m, 2H), 2.41 (t, J=7 Hz, 2H), 3.03 (br, 4H), 3.45 (t, J=7 Hz, 2H), 3.61 (br, 4H), 3.89 (s, 3H), 4.04 (s, 2H), 7.05 (d, J=10 Hz, 2H), 7.71 (d, J=10 Hz, 2H).

EXAMPLES 2-17

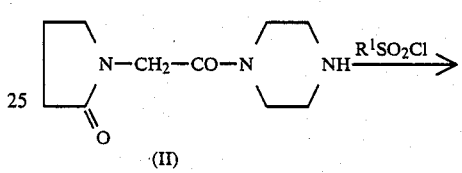

(II)

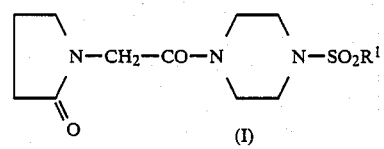

(I)

(wherein R$^1$ has the same meaning as defined above.)

In the same method as in Example 1, the reactions were carried out under the conditions shown in Table 1, and the objective compounds (I) were obtained. Their properties are shown in Table 2.

TABLE 1 (No. 1)

| Ex. No. | Amount of Compound (II) g (mmol) | R$^1$ | Amount of R$^1$SO$_2$Cl ml (mmol) | Amount of Et$_3$N ml (mmol) | Amount of CH$_2$Cl$_2$ (ml) | Reaction Time (hr., min.) | Yield (g) | Yield (%) | Compd. No. |
|---|---|---|---|---|---|---|---|---|---|
| 2 | 1.516 (6.40) | phenyl | 0.654 (5.12) | 0.715 (5.12) | 21 | 1'40" | 1.200 | 66.7 | Ia-2 |
| 3 | 1.450 (6.124) | 4-Me-phenyl | 0.934 (4.90) | 0.683 (4.90) | 20 | 1'45" | 1.069 | 59.7 | Ia-3 |
| 4 | 1.062 (5.03) | 4-Cl-phenyl | 1.167 (5.53) | 0.771 (5.53) | 15 | 2'45" | 1.707 | 88.0 | Ia-4 |
| 5 | 1.036 (4.90) | 4-F-phenyl | 1.050 (5.39) | 0.752 (5.39) | 16 | 16' | 1.586 | 87.5 | Ia-5 |

TABLE 1-continued
(No. 1)

| Ex. No. | Amount of Compound (II) g (mmol) | Amount of R¹SO₂Cl R¹ | ml (mmol) | Amount of Et₃N ml (mmol) | Amount of CH₂Cl₂ (ml) | Reaction Time (hr., min.) | Yield (g) | (%) | Compd. No. |
|---|---|---|---|---|---|---|---|---|---|
| 6 | 1.519 (6.42) | —⟨C₆H₄⟩—NHAc | 2.016 (8.60) | 1.203 (8.60) | 21 | 3′ | 1.578 | 59.7 | Ia-6 |
| 7 | 1.757 (7.42) | —⟨C₆H₄⟩—NO₂ | 1.316 (5.94) | 0.828 (5.94) | 24 | 2′ | 1.567 | 65.9 | Ia-7 |
| 8 | 1.522 (6.43) | —CH=CH—⟨C₆H₅⟩ | 1.303 (6.43) | 0.897 (6.43) | 21 | 2′ | 1.017 | 41.9 | Ia-8 |

TABLE 1
(No. 2)

| Ex. No. | Amount of Compound (II) g (mmol) | Amount of R¹SO₂Cl R¹ | ml (mmol) | Amount of Et₃N ml (mmol) | Amount of CH₂Cl₂ (ml) | Reaction Time (hr., min.) | Yield (g) | (%) | Compd. No. |
|---|---|---|---|---|---|---|---|---|---|
| 9 | 1.629 (6.88) | 1-naphthyl | 1.248 (5.50) | 0.768 (5.5) | 22 | 2′ | 1.502 | 67.7 | Ia-9 |
| 10 | 1.535 (6.48) | 2-naphthyl | 1.176 (5.19) | 0.724 (5.19) | 21 | 3′30″ | 1.248 | 59.9 | Ia-10 |
| 11 | 1.473 (6.22) | 2-thienyl | 1.273 (6.97) | 1.069 (7.65) | 20 | 1′30″ | 0.736 | 33.1 | Ia-11 |
| 12 | 1.390 (5.87) | —Me | 0.363 (4.70) | 0.654 (4.70) | 20 | 2′45″ | 0.743 | 54.6 | Ia-12 |
| 13 | 1.274 (5.38) | —Et | 0.459 (4.84) | 0.676 (4.84) | 18 | 1′40″ | 0.802 | 54.6 | Ia-13 |
| 14 | 1.299 (5.49) | -i-Pr | 0.554 (4.94) | 0.688 (4.94) | 18 | 3′ | 0.697 | 44.6 | Ia-14 |
| 15 | 1.534 (6.48) | -n-Bu | 0.672 (5.18) | 0.723 (5.18) | 21 | 2′30″ | 0.739 | 43.0 | Ia-15 |
| 16 | 0.495 (2.34) | 3-pyridyl | 0.495 (2.81) | 0.389 (2.81) | 9 | 1′30″ | 0.785 | 95.1 | Ia-16 |

TABLE 1-continued

| | Amount of Compound (II) | Amount of R¹SO₂Cl (No. 2) | | Amount of Et₃N | Amount of CH₂Cl₂ | Reaction Time | Yield | | Compd. |
|---|---|---|---|---|---|---|---|---|---|
| Ex. No. | g (mmol) | R¹ | ml (mmol) | ml (mmol) | (ml) | (hr., min.) | (g) | (%) | No. |
| 17 | 0.600 (2.84) | $-N\begin{smallmatrix}Me\\Me\end{smallmatrix}$ | 0.428 (3.98) | 0.633 (4.54) | 11 | 2'23" | 0.779 | 86.1 | Ia-17 |

TABLE 2

| Compd. No. | m.p. (°C.) | Recrystallizing Solvent | Molecular Formula | Elementary Analysis (%) up: Calcd. down: Found | | | | IR (cm$^{-1}$) | NMR |
|---|---|---|---|---|---|---|---|---|---|
| | | | | C | H | N | S / Cl | | |
| I a-2 | 152.0~153.0 | acetone-Et$_2$O | C$_{16}$H$_{21}$N$_3$O$_4$S | 54.68 / 54.62 | 6.02 / 6.03 | 11.96 / 11.84 | S 9.12 / 8.93 | (Nujol) 3505, 3410, 3100, 3060, 3035, 1686, 1652, 1496, 1475, 1459, 1446, 1417 | δ(CDCl$_3$): 2.04 (q,J = 7Hz,2H); 2.37 (t, J = 7Hz,2H); 3.02 (t,J = 6Hz,4H); 3.42 (t,J = 7Hz,2H); 3.62 (br.s, 4H); 4.02 (s,2H); 7.5–7.8 (m, 5H) |
| I a-3 | 189.5~190.5 | acetone-Et$_2$O | C$_{17}$H$_{23}$N$_3$O$_4$S | 55.87 / 55.81 | 6.34 / 6.40 | 11.50 / 11.34 | S 8.77 / 8.53 | (Nujol) 3075, 1689, 1670, 1657, 1599, 1493, 1458, 1408 | δ(CDCl$_3$): 1.95–2.48 (m,4H); 2.43 (s,3H); 2.99 (t,J = 6Hz,4H); 3.42 (t, J = 7Hz,2H); 3.60 (br.s,4H); 4.01 (s,2H); 7.33 (d,J = 9Hz, 2H); 7.12 (d,J = 9Hz,2H) |
| I a-4 | 186.5~187.5 | MeOH | C$_{16}$H$_{20}$N$_3$O$_4$ClS | 49.80 / 49.63 | 5.22 / 5.25 | 10.89 / 10.91 | S 8.31 / 8.23; Cl 9.19 / 9.26 | (Nujol) 3505, 3382, 3090, 3020, 1687, 1653, 1588, 1569, 1594, 1472, 1453, 1444, 1408 | δ(CDCl$_3$–CD$_3$OD 4:1 v/v) 1.9–2.2 (m,2H); 2.42 (t,J = 7Hz, 2H); 3.06 (br.s,4H); 3.46 (t, J = 7Hz,2H); 3.63 (br.s,4H); 4.06(s,2H); 7.74 (d,J = 9Hz,2H); 7.57 (d,J = 9Hz,2H) |
| I a-5 | 194.0~195.0 | MeOH | C$_{16}$H$_{20}$FN$_3$O$_4$S | 52.02 / 51.80 | 5.46 / 5.28 | 11.38 / 11.34 | S 8.68 / 8.69 | (Nujol) 3105, 3060, 3040, 1687, 1650, 1587, 1496, 1476, 1460, 1446, 1433, 1412 | δ(CDCl$_3$–CD$_3$OD = 4:1 v/v): 2.10 (q,J = 7Hz,2H); 2.40 (t, J = 7Hz,2H); 3.05 (br.s,4H); 3.46 (t,J = 7Hz,2H); 3.63 (br.s, 4H); 4.05 (s,2H); 7.2–7.9 (m, 4H) |
| I a-6 | 217.5~218.5 | CH$_2$Cl$_2$—Et$_2$O | C$_{18}$H$_{24}$N$_4$O$_5$S.1/5H$_2$O | 52.47 / 52.41 | 5.97 / 5.85 | 13.60 / 13.34 | S 7.78 / 7.83 | (Nujol) 3317, 3280, 3225, 3197, 3115, 3027, 3020, 1705, 1696, 1637, 1594, 1534, 1497, 1471, 1451, 1413, 1403 | δ(CDCl$_3$–CD$_3$OD = 5:1 v/v): 1.90–2.20 (m,2H); 2.17 (s,3H); 2.40 (t,J = 7Hz,2H); 3.00 (br.s, 4H); 3.43 (t,J = 7Hz,2H); 3.60 (br.s,4H); 4.03 (s,2H); 7.67, 7.77 (A$_2$B$_2$,J = 10Hz,4H) |
| I a-7 | 229.0~230.0 | CH$_2$Cl$_2$—Et$_2$O | C$_{16}$H$_{20}$N$_4$O$_6$S.1/5H$_2$O | 48.04 / 48.03 | 5.14 / 5.02 | 14.01 / 13.91 | S 8.02 / 7.94 | (Nujol) 3107, 3070, 1698, 1663, 1607, 1527, 1493, 1455, 1425, 1403 cm$^{-1}$ | δ(CDCl$_3$–CD$_3$OD = 4:1 v/v): 2.10 (q,J = 7Hz,2H); 2.40 (t, J = 7Hz,2H); 3.12 (br.s,4H); 3.44 (t,J = 7Hz,2H); 3.63 (br. 4H); 4.04 (s,2H); 7.98 (d, J = 9Hz,2H); 8.42 (d,J = 9Hz,2H) |
| I a-8 | 202.0~203.5 | acetone-Et$_2$O | C$_{18}$H$_{23}$N$_3$O$_4$S | 57.28 / 56.99 | 6.14 / 6.17 | 11.13 / 10.84 | S 8.49 / 8.40 | (Nujol) 3039, 3023, 1697, 1648, 1497, 1469, 1463, 1453, 1418 | δ(CDCl$_3$): 1.90–2.20 (m,2H); 2.39 (t, J = 7Hz,2H); 3.20 (t,J = 6Hz,4H); 3.46 (t,J = 7Hz,2H); 3.62 (br.s, 4H); 4.07 (s,2H); 6.66 (d, J = 16Hz,1H); 7.47 (d,J = 16Hz, 1H); 7.44 (s,5H) |
| I a-9 | 203.5~204.5 | CH$_2$Cl$_2$—Et$_2$O | C$_{20}$H$_{23}$N$_3$O$_4$S.1/10H$_2$O | 59.57 / 59.52 | 5.80 / 5.70 | 10.42 / 10.32 | S 7.95 / 7.89 | (Nujol) 3120, 3065, 3030, 1688, 1648, 1613, 1598, 1509, 1499, 1471, 1459, 1448, 1444, 1426, 1415 | δ(CDCl$_3$): 2.02 (q,J = 7Hz,2H); 2.34 (t, J = 7Hz,2H); 3.17 (t,J = 6Hz,4H); 3.40 (t,J = 7Hz,2H); 3.55 (br.s, 4H); 7.46–8.8 (m,7H) |

TABLE 2-continued

| Compd. No. | m.p. (°C.) | Recrystallizing Solvent | Molecular Formula | Elementary Analysis (%) up: Calcd. down: Found | | | | IR (cm⁻¹) | NMR |
|---|---|---|---|---|---|---|---|---|---|
| | | | | C | H | N | S/Cl | | |
| I a-10 | 181.0~182.0 | acetone-Et₂O | C₂₀H₂₃N₃O₄S | 59.83 59.94 | 5.77 5.79 | 10.47 10.54 | 7.99 7.91 | (CHCl₃) 1681, 1667, 1591, 1503, 1492, 1463, 1448, 1440, 1424, 1409 | δ(CDCl₃): 2.04 (q,J = 7Hz,2H); 2.33 (t, J = 7Hz,2H); 3.06 (t,J = 7Hz,4H); 3.38 (t,J = 7Hz,2H); 3.60 (br.s, 4H); 3.97 (s,2H); 7.56-8.32 (m,7H) |
| I a-11 | 142.5~143.5 | acetone-Et₂O | C₁₄H₁₉N₃O₄S₂ | 47.04 46.90 | 5.36 5.33 | 11.76 11.64 | 17.94 17.99 | (Nujol) 3080, 3070, 1689, 1677, 1656, 1497, 1468, 1451, 1430, 1426, 1401 | δ(CDCl₃): 2.06 (q,J = 7Hz,2H); 2.39 (t, J = 7Hz,2H); 3.07 (t,J = 6Hz,4H); 3.46 (t,J = 7Hz,2H); 3.65 (br.s, 4H); 4.06 (s,2H); 7.10-7.75 (m,3H) |
| I a-12 | 147.0~148.5 | acetone-Et₂O | C₁₁H₁₉N₃O₄S | 45.66 45.74 | 6.62 6.51 | 14.52 14.46 | 11.08 11.05 | (Nujol) 3020, 1687, 1660, 1492, 1461, 1447, 1432, 1406 | δ(CDCl₃): 2.12 (q,J = 7Hz,2H); 2.42 (t, J = 7Hz,2H); 2.79 (s,3H); 3.22 (br,4H); 3.50 (t,J = 7Hz,2H); 3.65 (br,4H); 4.10 (s,2H) |
| I a-13 | 154.5~155.5 | acetone-Et₂O | C₁₂H₂₁N₃O₄S | 47.51 47.32 | 6.98 6.82 | 13.85 13.77 | 10.57 10.42 | (Nujol) 2996, 1691, 1660, 1498, 1475, 1457, 1440, 1408 | δ(CDCl₃): 1.35 (t,J = 7.5Hz,3H); 1.99-2.55 (m,4H); 2.98 (q,J = 7.5Hz,2H); 3.3 (br.4H); 3.52 (t,J = 7Hz, 2H); 3.6 (br.4H); 4.12 (s,2H) |
| I a-14 | 121.0~123.0 | acetone-Et₂O | C₁₃H₂₃N₃O₄S | 49.19 49.19 | 7.30 7.24 | 13.24 13.17 | 10.10 10.29 | (Nujol) 1692, 1668, 1493, 1469, 1457, 1449, 1428, 1407 | δ(CDCl₃): 1.34 (d,J = 7Hz,6H); 2.12 (q, J = 7Hz,2H); 2.42 (t,J = 7Hz,2H); 3.19 (quintet,J = 7Hz,1H); 3.3-3.7 (m,10H); 4.09 (s,2H) |
| I a-15 | 110.0~111.0 | acetone-Et₂O | C₁₄H₂₆N₃O₄S | 50.74 50.61 | 7.60 7.56 | 12.68 12.61 | 9.67 9.70 | (Nujol) 1687, 1663, 1653, 1498, 1468, 1458, 1448, 1412 | δ(CDCl₃): 0.93 (t,J = 7Hz,3H); 1.2-2.6 (m, 8H); 2.43 (t,J = 7Hz,2H); 3.2-3.8 (m,10H); 4.11 (s,2H) |
| I a-16 | 174.5~175.0 | CH₂Cl₂-Et₂O | C₁₆H₂₀N₄O₄S | 51.12 50.95 | 5.72 5.72 | 15.89 15.79 | 9.10 8.88 | (Nujol) 3063, 1692, 1648, 1612, 1576, 1566, 1488, 1462, 1449, 1418, 1411 (sh) (sh): shoulder | δ(CDCl₃): 2.10 (q,J = 7Hz,2H); 2.35 (t, J = 7Hz,2H); 3.10 (t,J = 6Hz,4H); 3.45 (t,J = 7Hz,2H); 3.65 (br. 4H); 4.05 (s,2H); 7.51 (d–d, J₁ = 9Hz,J₂ = 6Hz,1H); 8.05 (splited d,J = 9Hz,1H); 8.86 (br.d,J = 6Hz,1H); 9.00 (br.s, 1H) |
| I a-17 | 147.0~148.0 | CH₂Cl₂-Et₂O | C₁₂H₂₂N₄O₄S | 45.27 45.13 | 6.96 6.83 | 17.60 17.48 | 10.07 9.88 | (CHCl₃) 1683, 1668, 1493, 1464, 1448, 1425, 1410 | δ(CDCl₃): 1.90-2.23 (m,2H); 2.43 (t, J = 7Hz,2H); 3.20-3.75 (m,10H); 4.10 (s,2H) |

EXAMPLE 18

1-Methylcarbamoyl-4-[(2-oxopyrrolidin-1-yl)acetyl]-piperazine (Ib-1)

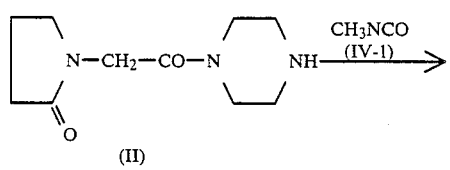

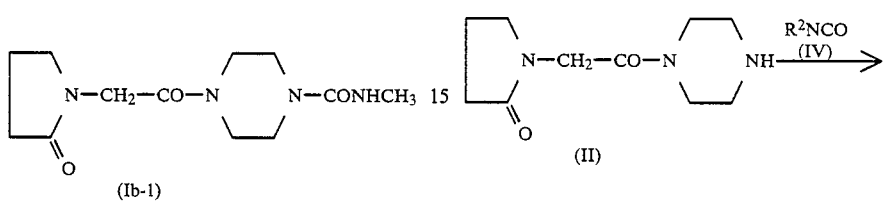

700 mg (3.31 mmol) of (2-oxopyrrolidin-1-yl)acetyl-piperazine was dissolved in 10.5 ml of $CH_2Cl_2$, and 0.215 ml (3.64 mmol) of methyl isocyanate was added to the mixture under ice-cooling, and the mixture was warmed to room temperature and stirred for 1 hr. After evaporating $CH_2Cl_2$, the precipitated crystals were washed with $Et_2O$ and collected by filtration. By recrystallizing from $EtOH-Et_2O$, 856 mg of the objective compound (yield: 96.3%) was obtained as colorless prisms.

m.p.: 203.0°–205.0° C.

Anal. Calcd. (%) for $C_{12}H_{20}N_4O_3$: C, 53.72; H, 7.51; N, 20.88. Found (%): C, 53.77; H, 7.53; N, 20.69.

IR (Nujol): 3347, 1681, 1658, 1620, 1552, 1492, 1469, 1454, 1411, 1398 ($cm^{-1}$).

NMR ($CDCl_3-CD_3OD=4:1$ v/v): δ 2.14 (q, J=7 Hz, 2H); 2.46 (t, J=7 Hz, 2H); 2.77 (s, 3H), 3.37–3.60 (m, 10H); 4.13 (s, 2H).

EXAMPLES 19–22

(wherein $R^2$ has the same meaning as defined above.)

In the same method as in Example 17, the reactions were carried out under the conditions shown in Table 3, whereby the objective compounds (Ib) were obtained. Their properties are shown in Table 4.

TABLE 3

| Ex. No. | Amount of Compd. (II) g (mmol) | $R^2$ | Amount of $R^2NCO$ ml (mmol) | Amount of $CH_2Cl_2$ (ml) | Reaction Time (hr., min.) | Yield (g) | Yield (%) | Compd. No. |
|---|---|---|---|---|---|---|---|---|
| 19 | 0.70 (3.31) | n-Bu | 0.411 (3.64) | 10.5 | 1' | 0.949 | 92.3 | Ib-2 |
| 20 | 1.50 (7.10) | ⟨C₆H₄⟩-OMe | 1.012 (7.81) | 23 | 16' | 2.419 | 94.5 | Ib-3 |
| 21 | 1.00 (4.73) | ⟨C₆H₄⟩-F | 0.592 (5.20) | 15 | 55" | 1.597 | 96.8 | Ib-4 |
| 22 | 0.70 (3.31) | naphthyl | 0.524 (3.64) | 10.5 | 55" | 1.226 | 97.2 | Ib-5 |

TABLE 4

| Compd. No. | m.p. (°C.) | Recrystallizing Solvent | Molecular Formula | Elementary Analysis (%) up: Calcd. down: Found C | H | N | F | IR ($cm^{-1}$) | NMR |
|---|---|---|---|---|---|---|---|---|---|
| Ib-2 | 132.0–133.0 | $CH_2Cl_2-Et_2O$ | $C_{15}H_{26}N_4O_3$ | 58.04 / 58.11 | 8.44 / 8.56 | 18.05 / 18.08 | | (Nujol) 3293, 3072, 1700, 1648, 1627, 1548, 1491, 1468, 1449, 1412 (Nujol) | ($CDCl_3$) 0.91 (t,J = Hz,3H); 1.20–1.60 (m,4H); 2.12 (q,J = 7Hz,2H); 2.42 (t,J = 7Hz, 2H); 3.10–3.60 (m,12H); 4.11 (s,2H); 4.90 (t, J = 7Hz,1H) ($CDCl_3-CD_3OD$ = 4:1 v/v) |

TABLE 4-continued

| Compd. No. | m.p. (°C.) | Recrysta-llizing Solvent | Molecular Formula | Elementary (%) Analysis up: Calcd. down: Found | | | | IR (cm$^{-1}$) | NMR |
|---|---|---|---|---|---|---|---|---|---|
| | | | | C | H | N | F | | |
| I b-3 | 181.0~182.0 | Et$_2$O | C$_{18}$H$_{24}$N$_4$O$_4$ | 59.99 59.84 | 6.71 6.67 | 15.55 15.39 | | 3347, 1678, 1657, 1602, 1541, 1512, 1490, 1464, 1448, 1412 (Nujol) | 2.14 (q,J = 7Hz,2H); 2.46 (t, J = 7Hz,2H); 3.54 (br.s,10H); 3.79 (s,3H); 4.13 (s,2H); 6.86, 7.25 (A$_2$B$_2$,J = 9Hz,4H) (CDCl$_3$-CD$_3$OD = 4:1 v/v) |
| I b-4 | 201.0~204.0 | CH$_2$Cl$_2$-Et$_2$O | C$_{17}$H$_{21}$N$_4$O$_2$F | 58.61 58.40 | 6.08 6.04 | 16.08 15.92 | 5.45 5.65 | 3350, 1671, 1652, 1609, 1542, 1509, 1489, 1463, 1452, 1442, 1409 (Nujol) | 2.15 (q,J = 7Hz,2H); 2.47 (t, J = 7Hz,2H); 3.56 (br.s,10H); 4.13 (s,2H); 6.97 (t,J = 9Hz, 2H); 7.35 (d—d,J$_1$ = 9Hz,J$_2$ = 5z, 2H) (CDCl$_3$) |
| I b-5 | 216.0~218.0 | CH$_2$Cl$_2$-Et$_2$O | C$_{21}$H$_{24}$N$_4$O$_3$ | 66.29 66.04 | 6.36 6.45 | 14.73 14.67 | | 3230, 3055, 1696, 1647, 1632, 1622, 1599, 1576, 1521, 1507, 1463, 1449, 1433, 1403 (Nujol) | 2.05 (q,J = 7Hz,2H); 2.35 (t, J = 7Hz,2H); 3.25-3.50 (m,10H); 3.93 (s,2H); 7.3-7.9 (m,7H) (CDCl$_3$) |

EXAMPLE 23

1-[(2-Oxopyrrolidin-1-yl)acetyl]-4-hydrazinocarbonyl-piperazine (Ib-5)

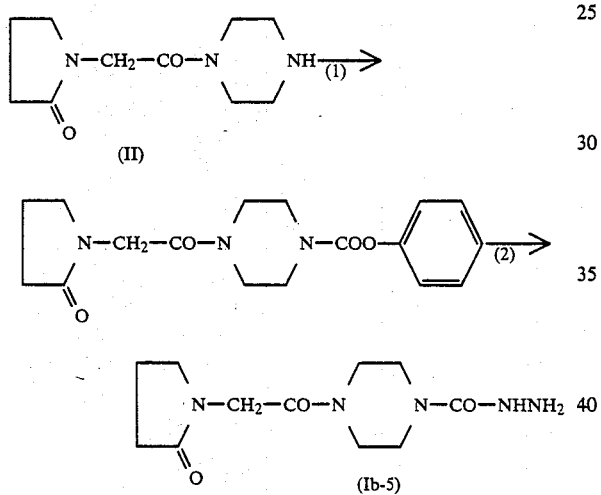

(1) 5.026 g (23.790 mmol) of [(2-oxopyrrolidin-1-yl)acetyl]piperazine was dissolved in 90 ml of dichloromethane, and 3.283 ml (26.169 mmol) of phenyl chloroformate and 3.982 ml (28.982 mmol) of triethylamine were added to the mixture with stirring under ice-cooling. After 10 min., the mixture was warmed to room temperature and stirred for 1 hr. The reaction solution was washed with diluted HCl, aqueous NaHCO$_3$, and water, respectively. After drying, the solvent was distilled off. The residue was washed with Et$_2$O and recrystallized from CH$_2$Cl$_2$-Et$_2$O, whereby 7.710 g of the objective compound (yield: 97.8%) was obtained as prisms melting at 185.0°-186.0° C.

Anal. Calcd. (%) for C$_{17}$H$_{21}$N$_3$O$_4$: C, 61.62; H, 6.39; N, 12.68. Found (%): C, 61.56; H, 6.40; N, 12.65.

IR (Nujol): 1722, 1679, 1661, 1592, 1494, 1460, 1443, 1419 cm$^{-1}$.

IR (CHCl$_3$): 1719, 1682, 1664, 1594, 1495, 1461, 1421 cm$^{-1}$.

NMR (CDCl$_3$): δ 2.12 (quintet, J=7 Hz, 2H), 2.43 (t, J=7 Hz, 2H), 3.30-3.85 (m, 10H), 4.12 (s, 2H), 7.00-7.50 (m, 5H).

(2) To 3.380 g (10.200 mmol) of 1-phenoxycarbonyl-4-(2-oxopyrrolidin-1-yl)acetylpiperazine was added 10 ml of hydrazine hydrate (100%), and the mixture was stirred for 30 min. at 90° C. Under the reduced pressure, the solution was concentrated, and the residue was subjected to silica gel column chromatography (silica gel: 273.9 g), and eluted with a solution of CHCl$_3$—MeOH-concentrated aqueous ammonia (32:6:1 v/v/v), whereby 1.302 g of the tilted compound (yield: 46.8%) was obtained as prisms.

m.p.: 164.0°-166.0 (°C.) (recrystallized from i-propyl alcohol).

Anal. Calcd. (%) for C$_{11}$H$_{19}$N$_5$O$_3$.1/5H$_2$O: C, 48.41; H, 7.17; N, 25.66. Found (%): C, 48.35; H, 7.12; N, 25.88.

IR (Nujol): 3200, 1683, 1648, 1510, 1500, 1454, 1412 cm$^{-1}$.

NMR (CDCl$_3$—CD$_3$OD=10:1 v/v): δ (2.09 (quintet, 2H), 2.44 (t, 2H, J=7 Hz), 3.20-3.80 (m, 10H), 4.11 (s, 2H).

REFERENTIAL EXAMPLE (2-Oxopyrrolidin-1-yl)acetylpiperazine

To 18,133 g (115 mmol) of methyl 2-oxo-1-pyrrolidinyl acetate was added 19.778 g (230 mmol) of piperazine, and the mixture was heated at 100° C. for 2 hours and 20 minutes. After evaporating the excess piperazine under the reduced pressure, the residue was subjected to silica gel column chromatography and eluted with a mixture of CHCl$_5$—MeOH-concentrated aqueous ammonia (32:4:0.5 to 32:6:1 v/v/v). The eluted fraction was concentrated under the reduced pressure, whereby 16.856 g of the objective compound (yield: 69.1%) was obtained as crystals.

m.p.: 116.0-117.0 (°C.). (recrystallized from i-propanol—Et$_2$O).

Anal. Calcd. (%) for C$_{10}$H$_{17}$N$_3$O$_2$: C, 56.85; H, 8.11; N, 19.89. Found (%): C, 56.74; H, 8.08; N, 19.75.

IR (Nujol): 3295, 1676, 1642, 1488, 1463, 1451, 1436, 1408 cm$^{-1}$.

NMR (CDCl$_3$): δ 1.87 (br. s. 1H; eliminated by addition of CD$_3$OD), 1.95-2.25 (m, 2H), 2.43 (t, J=7 Hz, 2H), 3.84 (t, J=6 Hz, 4H), 3.4-3.6 (m, 6H), 4.10 (s, 2H).

Experiment

Prevention against the ECS-Induced Amnesia in Mice

The test apparatus was a black acrylic resin box (30×30×30 cm) with an electrifiable grid floor in which a white wooden platform (10×10×1 cm) was placed in one corner. The step-down passive avoidance test was conducted on 3 groups of 10 SD mice each (male, 4 to 5 weeks age). A solvent was orally administered to the animals of the first group as a control group and the test compounds at doses of 5 and 50 mg/kg were orally given to other 2 groups 60 min. before the acquisition trial. In the acquisition trail, mice were individually placed on the platform and a scrambled foot shock (3 mA, for 5 sec.) was delivered through the grid floor as soon as the mouse moved off the platform. Five to ten min. after the foot shock, a single electroconvulsive shock (30 mA, 100 Hz (rectangular wave), for 0.2 sec.) was administered transcorneally and then each animal was placed in the home cage. After 24 hr. later, each mouse was again placed on the platform and the latency for descending on the grid floor was measured. A long latency in the retention test indicates good acquisition. The step-down latencies were evaluated using the Mann-Whitney U-test.

In Table 5, the results were shown as percent change in latencies over control defined as 100.

TABLE 5

| Effects of Compounds against Amnesia Induced by Electro Convulsive Shock | | |
|---|---|---|
| Compound No. | 5 mg/kg | 50 mg/kg |
| Ia - 4 | 176** | 70 |
| 5 | 244** | 265* |
| 8 | 226*** | 181* |
| 9 | 158** | 83 |
| Ib - 5 | 232*** | 340*** |

*$p < 0.05$ $p < 0.025$ *$p < 0.01$

What we claim is:

1. A compound of the formula

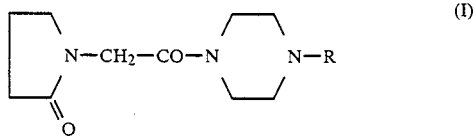 (I)

wherein R is $-SO_2R^1$ or $-CONHR^2$; $R^1$ is methyl, ethyl, isopropyl, n-butyl, dimethylamino, pyridyl, thienyl, phenylethenyl, or naphthyl; and $R^2$ is methyl, n-butyl, fluorophenyl, metoxyphenyl, naphthyl or amino.

2. The compound claimed in claim 1, namely 1-[(2-oxopyrrolidine-1-yl)acetyl]-4-methylsulfonylpiperazine.

3. The compound claimed in claim 1, namely 1-[(2-oxopyrrolidine-1-yl)acetyl]-4-ethylsulfonylpiperazine.

4. The compound claimed in claim 1, namely 1-[(2-oxopyrrolidine-1-yl)acetyl]-4-isopropylsulfonylpiperazine.

5. The compound claimed in claim 1, namely 1-[(2-oxopyrrolidine-1-yl)acetyl]-4-n-butylsulfonylpiperazine.

6. The compound claimed in claim 1, namely 1-[(2-oxopyrrolidine-1-yl)acetyl]-4-dimethylaminosulfonylpiperazine.

7. The compound claimed in claim 1, namely 1-[(2-oxopyrrolidine-1-yl)acetyl]-4-[(2-phenylethenyl)sulfonyl]piperazine.

8. The compound claimed in claim 1, namely 1-[(2-oxopyrrolidine-1-yl)acetyl]-4-pyridylsulfonylpiperazine.

9. The compound claimed in claim 1, namely 1-[(2-oxopyrrolidine-1-yl)acetyl]-4-thienylsulfonylpiperazine.

10. The compound claimed in claim 1, namely 1-[(2-oxopyrrolidine-1-yl)acetyl]-4-(1-naphthylsulfonyl)piperazine.

11. The compound claimed in claim 1, namely 1-[(2-oxopyrrolidine-1-yl)acetyl]-4-(2-naphthylsulfonyl)piperazine.

12. The compound claimed in claim 1, namely 1-methylcarbamoyl-4-[(2-oxopyrrolidine-1-yl)acetyl]piperazine.

13. The compound claimed in claim 1, namely 1-n-butylcarbamoyl-4-[(2-oxopyrrolidine-1-yl)acetyl]piperazine.

14. The compound claimed in claim 1, namely 1-[(2-oxopyrrolidin-1-yl)acetyl]-4-hydrazinocarbonylpiperazine.

15. The compound claimed in claim 1, namely 1-[N-(4-fluorophenyl)-carbamoyl]-4-[(2-oxopyrrolidine-1-yl)acetyl]piperazine.

16. The compound claimed in claim 1, namely 1-[N-(4-methoxyphenyl)-carbamoyl]-4-[(2-oxopyrrolidine-1-yl)acetyl]piperazine.

17. The compound claimed in claim 1, namely 1-[N-(4-(1-naphthyl))-carbamoyl]-4-[(2-oxopyrrolidine-1-yl)acetyl]piperazine.

18. A pharmaceutical composition for the treatment of amnesia comprising a pharmacologically effective amount of a compound according to claim 1 together with a pharmaceutically acceptable carrier.

* * * * *